United States Patent [19]

Diaz-Collier et al.

[11] Patent Number: 5,212,091

[45] Date of Patent: May 18, 1993

[54] METHOD OF PRODUCING TISSUE FACTOR PATHWAY INHIBITOR

[75] Inventors: Judy A. Diaz-Collier, St. Louis; Mark E. Gustafson, St. Charles; Tze-Chein Wun, St. Louis, all of Mo.

[73] Assignee: Monsanto Company, St. Louis, Mo.

[21] Appl. No.: 844,297

[22] Filed: Mar. 2, 1992

[51] Int. Cl.$^5$ ............................................. C12P 21/02
[52] U.S. Cl. ................................... 435/69.6; 530/380
[58] Field of Search ............................. 435/69.1, 69.6; 530/417

[56] References Cited

U.S. PATENT DOCUMENTS

| | | | |
|---|---|---|---|
| 4,421,685 | 12/1983 | Chance et al. | 530/303 |
| 4,511,502 | 4/1985 | Builder et al. | 530/417 |
| 4,512,922 | 4/1985 | Jones et al. | 530/408 |
| 4,656,249 | 4/1987 | Tregear et al. | 530/324 |
| 4,734,362 | 3/1988 | Hung et al. | 435/68.1 |
| 4,923,967 | 5/1990 | Bobbitt et al. | 530/351 |
| 4,966,852 | 10/1990 | Wun et al. | 435/320.1 |

OTHER PUBLICATIONS

Marston (1986) Biochem. J. 240:1–12.
Sofer (1984) Bio/Technology, pp. 1035–1038.
Novotny, et al (1989) J. Biol. Chem. 264: 18832–18837.
Wun et al., J. Biol. Chem. 263, 6001–6004 (1988).
Rapaport, Blood 73, 359–365 (1989).
Broze et al., Biochemistry 29, 7539–7546 (1990).
Day et al., Blood 76, 1538–1545 (1990).
Wun et al., J. Biol Chem. 265, 16096–16101 (1990).
Furman et al., Bio/Technoloy 5, 1047–1051 (1988).
Krueger et al., BioPharm. 2(3), pp. 40–45 (1989).

*Primary Examiner*—Robert A. Wax
*Attorney, Agent, or Firm*—Scott J. Meyer

[57] ABSTRACT

A method is disclosed for the production of tissue factor pathway inhibitor (TFPI) which comprises expression of a non-glycosylated form of TFPI in *E. coli* as host and obtaining a highly active TFPI by in vitro refolding of the protein in which inclusion bodies isolated from the *E. coli* cells are subjected to stepwise purification comprising either series (A) or series (B) as follows:

(A)
(1) subjecting the inclusion bodies to sulfitolysis to form TFPI-S-sulfonate,
(2) purifying TFPI-S-sulfonate by anion exchange chromatography,
(3) refolding TFPI-S-sulfonate by disulfide interchange reaction, and
(4) purifying active refolded TFPI by cation exchange chromatography, or (B)
(1) subjecting the inclusion bodies to reduction with β-mercaptoethanol in urea to form reduced TFPI,
(2) purifying the reduced TFPI by cation exchange chromatography,
(3) refolding reduced TFPI by disulfide interchange reaction in urea, and
(4) purifying the active refolded TFPI by cation exchange chromatography.

6 Claims, 14 Drawing Sheets

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 277 amino acids
        ( B ) TYPE: amino acid
        ( D ) TOPOLOGY: linear ( i i ) MOLECULE TYPE: protein ( x i ) SEQUENCE DESCRIPTION: SEQ ID NO:1:

```
Ala Asp Ser Glu Glu Asp Glu Glu His Thr Ile Ile Thr Asp Thr Glu
 1           5               10                  15

Leu Pro Pro Leu Lys Leu Met His Ser Phe Cys Ala Phe Lys Ala Asp
            20              25              30

Asp Gly Pro Cys Lys Ala Ile Met Lys Arg Phe Phe Phe Asn Ile Phe
            35              40              45

Thr Arg Gln Cys Glu Glu Phe Ile Tyr Gly Gly Cys Glu Gly Asn Gln
        50              55              60

Asn Arg Phe Glu Ser Leu Glu Glu Cys Lys Lys Met Cys Thr Arg Asp
65              70              75              80

Asn Ala Asn Arg Ile Ile Lys Thr Thr Leu Gln Gln Glu Lys Pro Asp
                85              90              95

Phe Cys Phe Leu Glu Glu Asp Pro Gly Ile Cys Arg Gly Tyr Ile Thr
            100             105             110

Arg Tyr Phe Tyr Asn Asn Gln Thr Lys Gln Cys Glu Arg Phe Lys Tyr
            115             120             125
```

-continued

| | | | | | | | | | | | | | | |
|---|---|---|---|---|---|---|---|---|---|---|---|---|---|---|
| Gly | Gly | Cys | Leu | Gly | Asn | Met | Asn | Asn | Phe | Glu | Thr | Leu | Glu | Cys |
| | 130 | | | | | 135 | | | | 140 | | | | |
| Lys | Asn | Ile | Cys | Glu | Asp | Gly | Pro | Asn | Gly | Phe | Gln | Val | Asp | Asn | Tyr |
| 145 | | | | | 150 | | | | | 155 | | | | 160 |
| Gly | Thr | Gln | Leu | Asn | Ala | Val | Asn | Asn | Ser | Leu | Thr | Pro | Gln | Ser | Thr |
| | | | | 165 | | | | | 170 | | | | | 175 |
| Lys | Val | Pro | Ser | Leu | Phe | Glu | Phe | His | Gly | Pro | Ser | Trp | Cys | Leu | Thr |
| | | | 180 | | | | | 185 | | | | | 190 | | |
| Pro | Ala | Asp | Arg | Gly | Leu | Cys | Arg | Ala | Asn | Glu | Asn | Arg | Phe | Tyr | Tyr |
| | | | 195 | | | | 200 | | | | | 205 | | | |
| Asn | Ser | Val | Ile | Gly | Lys | Cys | Arg | Pro | Phe | Lys | Tyr | Ser | Gly | Cys | Gly |
| | 210 | | | | | 215 | | | | | 220 | | | | |
| Gly | Asn | Glu | Asn | Asn | Phe | Thr | Ser | Lys | Gln | Glu | Cys | Leu | Arg | Ala | Cys |
| 225 | | | | | 230 | | | | | 235 | | | | | 240 |
| Lys | Lys | Gly | Phe | Ile | Gln | Arg | Ile | Ser | Lys | Gly | Gly | Leu | Ile | Lys | Thr |
| | | | | 245 | | | | | 250 | | | | | 255 | |
| Lys | Arg | Lys | Arg | Lys | Lys | Gln | Arg | Val | Lys | Ile | Ala | Tyr | Glu | Glu | Ile |
| | | | 260 | | | | | 265 | | | | | 270 | | |
| Phe | Val | Lys | Asn | Met | | | | | | | | | | | |
| | | | 275 | | | | | | | | | | | | |

( 2 ) INFORMATION FOR SEQ ID NO:2:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:2:

CATGGCTGAT TCTGAAGAAG ATGAAGAACA TACTA                                      35

( 2 ) INFORMATION FOR SEQ ID NO:3:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:3:

AGTGATAATA GTATGTTCTT CATCTTCTTC AGAATCAGC                                   39

( 2 ) INFORMATION FOR SEQ ID NO:4:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:4:

TTATCACTGA TACTGAACTG CCACCGCTGA AACTGATGCA                                 40

( 2 ) INFORMATION FOR SEQ ID NO:5:

( i ) SEQUENCE CHARACTERISTICS:
        ( A ) LENGTH: 28 base pairs
        ( B ) TYPE: nucleic acid
        ( C ) STRANDEDNESS: single -continued (D) TOPOLOGY: linear (ii) MOLECULE TYPE: DNA (synthetic)

(xi) SEQUENCE DESCRIPTION: SEQ ID NO:5:

TCAGTTTCAG CGGTGGCAGT TCAGTATC     28

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:6:

ATAACAAAGC TTACATATTT T     21

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:7:

ATATATCCAT GGCTGATTCT     20

(2) INFORMATION FOR SEQ ID NO:8:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:8:

GGATCCGCGG CAACAATTTC TACAAAACAC TTGACACTGT ATGAGCATGC AGTATAATTG     60

CTTC     64

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:9:

AATTGTGAGC GGATAACAAT T     21

METHOD OF PRODUCING TISSUE FACTOR PATHWAY INHIBITOR

BACKGROUND OF THE INVENTION

This invention relates to a novel method for the production of a blood coagulation inhibitor known as tissue factor pathway inhibitor (TFPI) and alternatively known as lipoprotein associated coagulation inhibitor (LACI).

Plasma contains a multivalent Kunitz-type inhibitor of coagulation, referred to herein as tissue factor pathway inhibitor (TFPI). This name has been accepted by the International Society on Thrombosis and Hemostasis, Jun. 30, 1991, Amsterdam. TFPI was first purified from a human hepatoma cell, Hep G2, as described by Broze and Miletich, *Proc. Natl. Acad. Sci. USA* 84, 1886–1890 (1987), and subsequently from human plasma as reported by Novotny et al., *J. Biol. Chem.* 264, 18832–18837 (1989); Chang liver and SK hepatoma cells as disclosed by Wun et al., *J. Biol. Chem.* 265, 16096–16101 (1990). TFPI cDNA have been isolated from placental and endothelial cDNA libraries as described by Wun et al., *J. Biol. Chem.* 263, 6001–6004 (1988); Girard et al., *Thromb. Res.* 55, 37–50 (1989). The primary amino acid sequence of TFPI, deduced from the cDNA sequence, shows that TFPI contains a highly negatively charged amino-terminus, three tandem Kunitz-type inhibitory domains, and a highly positively charged carboxyl terminus. The first Kunitz-domain of TFPI is needed for the inhibition of the factor $VII_a$/tissue factor complex and the second Kunitz-domain of TFPI is responsible for the inhibition of factor $X_a$ according to Girard et al., *Nature* 328, 518–520 (1989), while the function of the third Kunitz-domain remains unknown. See also copending application Ser. No. 07/301,779, filed Jan. 26, 1989, now allowed. TFPI is believed to function in vivo to limit the initiation of coagulation by forming an inert, quaternary factor $X_a$: TFPI: factor $VII_a$: tissue factor complex. Further background information on TFPI can be had by reference to the recent reviews by Rapaport, *Blood* 73, 359–365 (1989); Broze et al., *Biochemistry* 29, 7539–7546 (1990).

Recombinant TFPI has been expressed as a glycosylated protein using mammalian cell hosts including mouse C127 cells as disclosed by Day et al., *Blood* 76, 1538–1545 (1990), baby hamster kidney cells as reported by Pedersen et al., *J. Biol. Chem.* 265, 16786–16793 (1990), Chinese hamster ovary cells and human SK hepatoma cells. The C127 TFPI has been used in animal studies and shown to be effective in the inhibition of tissue factor-induced intravascular coagulation in rabbits according to Day et al., supra, and in the prevention of arterial reocclusion after thrombolysis in dogs as described by Haskel et al., *Circulation* 84, 821–827 (1991).

The cloning of the TFPI cDNA which encodes the 276 amino acid residue protein of TFPI is further described in Wun et al., U.S. Pat. No. 4,966,852, the disclosure of which is incorporated by reference herein.

BRIEF DESCRIPTION OF THE INVENTION

In accordance with the present invention a novel method for the production of tissue factor pathway inhibitor (TFPI) is provided. The method involves expression of a non-glycosylated form of TFPI in *E. coli* as host and obtaining a highly active TFPI by in vitro refolding of the protein. According to this method, the TFPI is produced by culturing, under fermentation conditions sufficient to produce said TFPI, *E. coli* host cells which have been transformed with a replicable expression vector containing the cDNA coding for said TFPI, harvesting the *E. coli* cells, isolating the inclusion bodies from the harvested *E. coli* cells and subjecting the inclusion bodies to a stepwise purification comprising, in an embodiment (A) of the invention:

(1) subjecting the inclusion bodies to sulfitolysis to form TFPI-S-sulfonate, (2) purifying TFPI-S-sulfonate by anion exchange chromatography, (3) refolding TFPI-S-sulfonate by disulfide interchange reaction, and (4) purifying active refolded TFPI by cation exchange chromatography.

In accordance with another embodiment (B) of the invention, the aforesaid inclusion bodies are subjected to a stepwise purification process comprising:

(1) subjecting the inclusion bodies to reduction with β-mercaptoethanol in urea to form reduced TFPI, (2) purifying the reduced TFPI by cation exchange chromatography, (3) refolding reduced TFPI by disulfide interchange reaction in urea, and (4) purifying the active refolded TFPI by cation exchange chromatography.

Illustrative ion exchange resins for use in the foregoing purification processes are conventional commercially available products such as, e.g., AG 501-X8 mixed bed ion exchanger from Bio Rad; MONO Q HR 5/5; MONO S HR 5/5; MONO S HR 10/10; and Hi-Load 10/16 Q Sepharose ion exchangers from Pharmacia.

Refolding of TFPI by reduction/re-oxidation and by sulfonation/disulfide interchange of the crude, solubilized inclusion bodies by procedures such as described in U.S. Pat. No. 4,923,967 resulted in very low activity. Unexpectedly, purification of TFPI prior to the refolding step by sulfonation followed by anion exchange chromatography according to embodiment (A) of the method of the invention resulted in a two-fold higher specific activity than a highly purified full-length SK hepatoma-derived TFPI in the inhibition of tissue factor-induced coagulation time assay as seen from EXAMPLE 1 hereinafter. This suggests that carbohydrates on TFPI are not required for its activity. These advantages of the *E. coli*-derived TFPI are surprising since the glycosylated SK hepatoma-derived TFPI was heretofore shown to have a significantly higher specific activity than TFPI isolated from other mammalian cell sources as reported by Wun et al., *J. Biol. Chem.* 265, 16096–16101 (1990).

Production of the TFPI in *E. coli* was further unexpected in that the TFPI is a highly structured protein of about 32,000 daltons in size and having 9 disulfide linkages (18 cys residues). A highly complex folding mechanism must be accomplished. There are few, if any, examples in the literature of such complex proteins produced in *E. coli* at final production yields of over 10 mg/liter of fermentation broths. In accordance with the present invention expression levels of over 100 mg/ml have been achieved with the *E. coli* expression system. By comparison, production of another highly structured protein, renin, of comparable molecular weight was not achieved in *E. coli*.

Another advantage of the present invention is that a substantially greater level of homogeneity of TFPI product is obtained than with the SK hepatoma-derived material which exhibits significant heterogeneity. Protein heterogeneity can result in an increased possibility for toxicity, immunogenicity and side effects. More complex and expensive purification processes are required to attempt to reduce heterogeneity. Analytical and monitoring methodologies are less effective (e.g. electrospray mass spectral analysis) and more costly when heterogeneity exists. Several classes of heterogeneity have been observed to occur in TFPI produced from mammalian expression systems but not E. coli expression systems as follows:

A. Phosphorylation

Mammalian expression systems were observed to phosphorylate Ser-2 of TFPI to differing extents (a typical value of phosphorylation is 25% of the total TFPI produced). Phosphorylation does not affect prothrombin clotting activity. TFPI produced from E. coli expression systems is not phosphorylated. Electrospray mass spectral analysis shows SK Hep TFPI is a mixture of phosphorylated and nonphosphorylated species.

B. Proteolytically-induced internal Cleavages

TFPI produced from CHO, C-127 and SK Hep was routinely observed to contain species with internal proteolytic cleavages at internal sites such as Arg-199 and Arg-83. These cleavages are believed to be a consequence of the long time periods mammalian produced TFPI must be exposed to media proteases prior to harvesting. E. coli TFPI was observed to contain only a smaller amount of internal proteolytic cleavages. This is believed to be a consequence that TFPI is sequestered within E. coli in insoluble refractile bodies and these refractile bodies are washed free of cell proteases prior to the time they are solubilized.

C. Glycosylation

TFPI produced from CHO, C-127 and SK Hep is extensively glycosylated at multiple sites. Approximately 30% of the mass of mammalian produced TFPI is derived from carbohydrate. Proteolytic mapping, and mass spectral data have shown there is a high degree of heterogeneity at these glycosylation sites. E. coli produced TFPI is not glycosylated.

According to a preferred embodiment of the invention, an N-terminal alanine residue is engineered into the TFPI sequence in order to improve expression and effect complete processing in E. coli of what would otherwise be an N-terminal methionine residue. For convenience in nomenclature, the numbering system of the 276 amino acid sequence of TFPI (LACI) as previously published by Wun et al., J. Biol. Chem. 263, 6001-6004 (1988); Girard et al., Thromb. Res. 55, 37-50 (1989); and in U.S. Pat. No. 4,466,852, is retained herein and the N-terminal alanine residue is assigned −1. Thus, this preferred embodiment of the TFPI produced in E. coli is a 277 amino acid residue protein. As used herein, the term TFPI is meant to include both the 276 amino acid TFPI protein and the 277 amino acid ala-TFPI protein.

Preferred replicable expression vectors in which the cDNA coding for the TFPI can be inserted are those such as described, e.g., by Olins et al., Gene 73, 227-235 (1988), and Olins and Rangwala, J. Biol. Chem. 264, 16973-16976 (1989), which are pBR327 based plasmids that contain the recA promoter ($P_{rec}A$) and the ribosome-binding site, derived from bacteriophage T7 phage gene 10 leader (g10-L-RBS). Such vectors are known to be suitable for enhanced expression of foreign genes in E. coli. Illustrative examples of such vectors are plasmids pMON5557 and pMON5766 shown in FIGS. 11 and 12, respectively. The cDNA for TFPI as described, e.g., by Wun et al., J. Biol. Chem. 263, 6001-6004 (1988); Girard et al., Thromb. Res. 55, 37-50 (1989); and Wun et al., U.S. Pat. No. 4,966,852, can be inserted into these and other such vectors for expression of foreign genes in E. coli by conventional recombinant DNA procedures. See, e.g., Maniatis et al., Molecular Cloning: A Laboratory Manual, Cold Spring Harbor Laboratory, Cold Spring Harbor, N.Y. (1982). Plasmid pBR327 is a 3273 bp deletion derivative of the commercially available plasmid pBR322 as described by Soberon et al., Gene 9, 287-305 (1980) and is indexed as SYNP 327 in GenBank.

DETAILED DESCRIPTION OF THE INVENTION

While the specification concludes with claims particularly pointing out and distinctly claiming the subject matter regarded as forming the invention, it is believed that the invention will be better understood from the following detailed description of preferred embodiments taken in conjunction with the appended drawings, in which:

FIGS. 1A and 1B show the chromatography of sulfonated inclusion bodies on Mono Q HR5/5 anion exchange column. Inclusion bodies were solubilized and sulfonated as described in METHODS in EXAMPLE 1 hereinbelow. Two ml of sulfonated sample (equivalent to 20 mg wet weight of inclusion bodies) was loaded onto a Mono Q HR5/5 column pre-equilibrated in Q-buffer (20 mM Tris/HCl, pH 8, 6 M urea, and 0.01% Brij 35 non-ionic detergent) containing 0.15 M NaCl. The column was washed with 15 ml of the equilibration buffer and eluted with a 30-ml gradient (0.15-0.4 M NaCl) in Q-buffer. One ml fractions were collected. FIG. (1A) shows the Mono Q Chromatogram. Solid line, absorbance at 280 nm; dashed line, NaCl gradient. Fractions indicated by a thick bar (30-33) containing the majority of full length TFPI protein were pooled for refolding tests. FIG. (1B) shows the SDS-PAGE. Ten μl of indicated fractions were loaded on a 10-20% gradient gel for electrophoresis. The gel was stained with Coomassie blue. The lane marked by MW was loaded with molecular weight standards. Pre-column sample was loaded in the lane marked Pre-.

FIGS. 2A and 2B show the chromatography of sulfonated inclusion bodies on Hiload Q Sepharose 16/10 anion exchange column. Sulfonated inclusion bodies were prepared as described in METHODS in EXAMPLE I hereinbelow. Forty ml of sulfonated sample (equivalent to 0.56 g of wet weight of inclusion body) was loaded onto Hiload Q Sepharose 16/10 pre-equilibrated in Q-buffer containing 0.15 M NaCl. The column was washed with 240 ml of the equilibration buffer and then eluted with a 396-ml gradient (0.15-0.4 M NaCl) in Q-buffer. FIG. 2A shows the chromatography profile; solid line, absorbance at 280 nm; dashed line, NaCl gradient. Fractions indicated by a thick bar (43-50) were pooled for refolding. FIG. 2B shows SDS-PAGE. Ten μl of indicated fractions were loaded on a 10-20% gradient gel. The gel was stained by Coomassie blue after electrophoresis.

FIG. 3 is a graphical representation which shows the specific activity increase during sulfitolysis/refold of *E. coli* TFPI. The sulfonated full-length TFPI pool from HiLoad Q Sepharose was diluted to an absorbance of $A_{280\ nm}=0.07$ with Q-buffer containing 0.3 M NaCl. Solid L-cysteine was added to a final concentration of 2 mM. The solution was incubated at room temperature for 24 hours, diluted 1:1 with water, 1 mM L-cysteine added, and incubated at room temperature for another 24 hours and at 4° C. for up to 8 days. Tissue factor-induced coagulation time assay was used to measure the activity and was compared with that of a standard preparation of full-length SK hepatoma TFPI. Specific activity was obtained by comparing the clotting time of plasma supplemented with a 1:10 dilution of refold mixture with a standard curve of which the construction was based on the clotting of plasma supplemented with purified SK hepatoma TFPI. The values are averages of three preparations with standard deviations indicated in error bars.

FIGS. 4A and 4B show the fractionation of refold mixture by chromatography on Mono S HR5/5 cation exchange column. A 7-day refold solution was acidified to pH 4.5 by the addition of 10 mM acetic acid and concentrated 25 fold by ultrafiltration using Amicon YM10 membrane. Two ml of the concentrated sample was loaded onto a Mono S HR5/5 column pre-equilibrated with S-buffer (20 mM sodium phosphate, pH 6.4, 6 M urea). The column was washed with 10 ml of S-buffer and eluted with a 70-ml gradient consisting of 0–0.7 M NaCl in S-buffer. One ml fractions were collected. FIG. 4A shows the chromatography profile; solid line, absorbance at 280 nm; dashed line, NaCl gradient; closed circle, specific activity relative to fraction 52. Specific activities were determined using tissue factor-induced coagulation time assay by comparing with a standard curve constructed by plotting clotting time vs. concentration of fraction 52 in milli-absorbance unit per ml. FIG. 4B shows SDS-PAGE. Ten μl of the indicated fractions was loaded on a 10–20% gradient gel. The gel was stained by Coomassie blue after electrophoresis. MW is the lane loaded with molecular weight standards. The lane marked by pre- is the pre-column sample. The samples on the left of the molecular weight markers were not reduced and those on the right were reduced in sample buffer containing 3.3% 2-mercaptoethanol and boiled for 3 minutes before electrophoresis.

FIGS. 5A, 5B and 5C show the optimization of Mono S HR 5/5 cation exchange column chromatography of refold mixture. Two ml of refold mixture was acidified to pH 4.5 by the addition of 10 mM acetic acid and loaded onto a Mono S HR5/5 column pre-equilibrated in starting buffer. The starting buffer for FIG. 5(A) and FIG. 5(B) consists of S-buffer and that for FIG. 5(C) consists of S-buffer supplemented with 0.3 M NaCl. The column was washed with 10 ml of starting buffer followed by NaCl gradients as indicated in each panel. Solid lines, absorbance at 280 nm; closed circle, blank run. The NaCl gradients were 20 mM/ml for FIG. 5(A) and 10 mM/ml for FIG. 5(B). In FIG. 5(C), the column was washed with 10 ml of 0.3 M NaCl in S-buffers followed by a NaCl gradient of 10 mM/ml.

FIGS. 6A and 6B show the chromatography of refold mixture on Mono S HR10/16 cation exchange column. A refold mixture (1050 ml) was acidified to pH 4.5 by the addition of 10 mM acetic acid and was concentrated 75 fold by ultrafiltration using a YM10 membrane. The concentrate was loaded onto a Mono S HR10/16 column pre-equilibrated in S-buffer containing 0.3 M NaCl. The column was washed with 120 ml (15 column volumes) of the equilibration buffer and eluted with a 0.3–0.5 M NaCl gradient in S-buffer. FIG. 6A shows the chromatography profile; solid line, absorbance at 280 nm; dashed line, NaCl gradient. The thick bar indicates the fractions (20–25) pooled that contains majority of the TFPI activity. FIG. 6B shows SDS-PAGE. Lane 1, molecular weight standards; lane 2, fraction 20–25 pool in non-reducing buffer; lane 3, fraction 20–25 pool reduced in sample buffer containing 3.3% 2-mercaptoethanol and boiled for 3 minutes before electrophoresis.

FIG. 7 is a graphical representation which shows the inhibition of bovine factor $X_a$ by purified SK hepatoma TFPI and refolded *E. coli* TFPI. Full-length SK hepatoma TFPI was isolated by chromatography of cell conditioned medium on a monoclonal anti-TFPI-Ig coupled Sepharose 4B column and a Mono S column by conventional procedures. See, e.g. Day et al., *Blood* 76, 1538–1545 (1990), and Wun et al., *Thromb. Haemostas.*, In Press, (1992), for conventional immunochromatography on monoclonal anti-LACI-Ig-Sephrose 4B columns. Inhibition of bovine factor $X_a$ was measured by an amidolytic assay using Spectrozyme $X_a$ as substrate. The concentration of TFPI was estimated by amino acid analysis and absorbance measurement. A molar extinction coefficient, $E_{280\ nm}=2.90\times 10^4$, and molecular weights of 38,000 and 32,000 for SK TFPI and *E. coli* TFPI, respectively, were used for the calculation of the molarity of TFPI. The concentration of bovine factor $X_a$ as determined by the supplier (American Diagnostica) matches the value obtained by active site titration with p-nitrophenyl p'-guanidinobenzoate according to Wun et al., *J. Biol. Chem.* 265, 16096–16101 (1990). Open circle, *E. coli* TFPI; closed circle, SK TFPI.

FIG. 8 is a graphical representation which shows a comparison of the inhibitory activities of full-length SK hepatoma TFPI and refolded *E. coli* TFPI in the inhibition of tissue factor-induced coagulation of human plasma. The tissue factor-induced coagulation time assay was performed as described in METHODS in EXAMPLE I hereinbelow. TFPIs were quantitated by amino acid analysis and absorbance measurement at 280 nm in which 1 mA ($1\times 10^{-3}$ absorbance unit) of TFPI was found to be equivalent to 34.5 nM. Open circle, *E. coli* TFPI; closed circle, SK TFPI.

FIG. 9 shows the sodium dodecyl sulfate polyacrylamide gel electrophoresis (SDS-PAGE) analysis of the TFPI prepared by embodiments (A) and (B) of the method of the invention as described herein. The primary band of TFPI was identical on reduced and native gels. On native gels the TFPI produced by embodiment (A), EXAMPLE I, is seen to have a higher content of dimer species, whereas the TFPI produced by embodiment (B), EXAMPLE II, is seen to have a higher content of lower molecular weight (C-terminally truncated) species. Molecular weight lanes are shown on the left (2 columns) and the right (1 column) and molecular weight standards are indicated in kilodaltons (kDa) on the right hand side of FIG. 9.

In order to illustrate specific preferred embodiments in greater detail, the following exemplary laboratory preparative work was carried out, although it will be understood that the invention is not limited to these specific examples or the specific details described therein. EXAMPLE I illustrates embodiment (A) and EXAMPLE II illustrates embodiment (B) of the invention.

EXAMPLE I

Materials

Urea (sequenal grade) and Brij 35 non-ionic surfactant were obtained from Pierce. Mixed bed resin AG501-X8 ion exchanger was purchased from Bio Rad. Mono Q HR 5/5 and HiLoad Q Sepharose anion exchange resins, and Mono S HR 5/5 and Mono S HR 10/16 cation exchange resins were obtained from Pharmacia. Thromboplastin reagent (Simplastin Excele®) was from Organon Teknika Corp. Bovine factor $X_a$ and Spectrozyme $X_a$ were supplied by American Diagnostica, Inc. SDS-PAGE 10–20% gradient gel was obtained from integrated Separation Systems.

Methods

Expression vectors and cloning strategies

Figure 11:
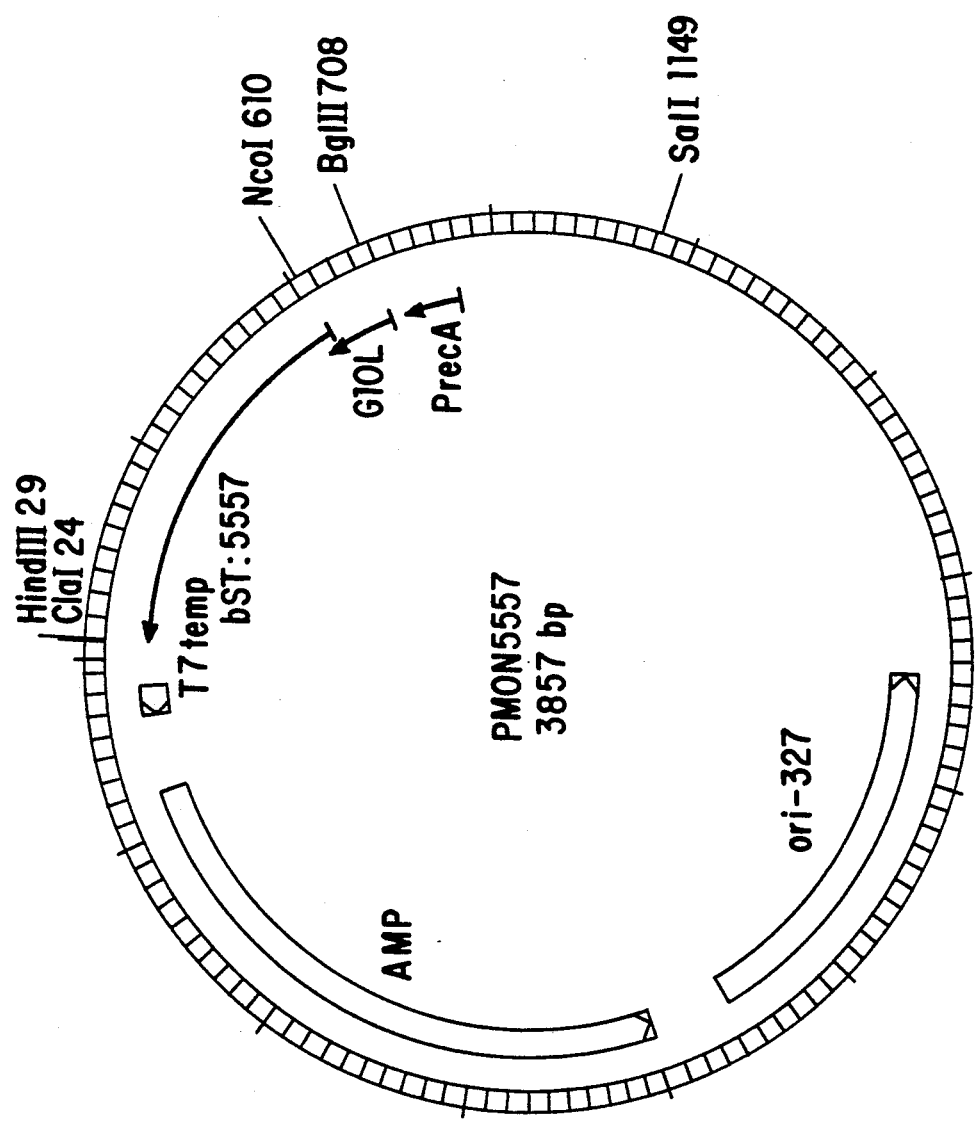
FIG. 11 is a diagrammatic representation that shows the map of plasmid pMON5557, which is a 3857 bp expression vector suitable for insertion of the TFPI cDNA. pMON5557 is a pBR327 based plasmid that contains the recA promoter (PrecA), a translational enhancer element and ribosome binding site derived from the gene 10 leader of bacteriophage T7 (G10L), and the T7 transcription terminator (T7 term).

A full length human TFPI cDNA [Wun et al., *J. Biol. Chem.* 263, 6001–6004 (1988)] was cloned into M13mp18 phage DNA cloning vector as a 1.4 Kb EcoRI fragment. Site-directed mutagenesis [oligonucleotide-directed in vitro mutagenesis system, version 2; Amersham] was used to introduce an NcoI site at the initiating ATG. The TFPI gene was then cloned as an NcoI/blunted MaeIII fragment into pMON5557 (FIG. 11) with NcoI and blunted HindIII ends resulting in the new vector pMON9308. MaeIII site is 15bp downstream from the stop codon in the TFPI cDNA. The expression vector contained the recA promoter, a translational enhancer element and ribosome binding site derived from the gene 10 leader of bacteriophage T7 as described by Olins and Rangwala, *J. Biol. Chem.* 264, 16973–16976 (1989), and the T7 transcription terminator. Plasmid pMON5557 also contains an irrelevant sequence, i.e. the bST gene (bovine somatotropin), which is replaced by the TFPI gene to form plasmid pMON9308.

Figure 12:
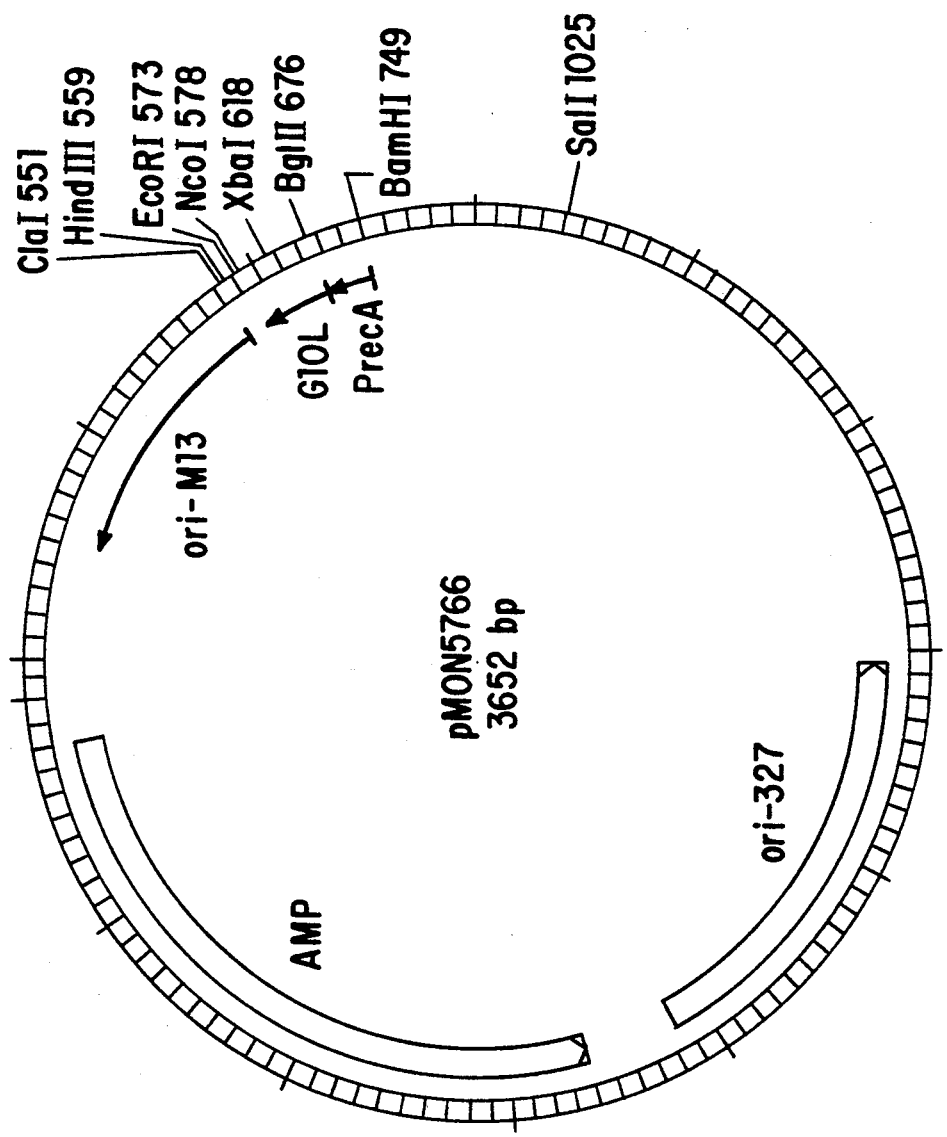
FIG. 12 is a diagrammatic representation that shows the map of plasmid pMON5766, which is a 3652 bp expression vector suitable for insertion of the TFPI cDNA. pMON5766 is a pBR327 based plasmid that contains PrecA, G10L, a multiple cloning site linker, and the M13 origin of replication (ori-M13).

The NcoI/NsiI fragment of pMON9308 was then replaced by a synthetic DNA fragment designed to (1) introduce an alanine encoding codon at the second position, (2) increase the A-T richness of the 5′ portion of the gene, and (3) improve *E. coli* codon usage. Four oligonucleotides, two for each strand, were used. All base substitutions (indicated in upper case), are silent changes. ECTFPI 2 and 3 were 5′ phosphorylated [Maniatis et al., *Molecular Cloning: A Laboratory Manual*, Cold Spring Harbor Laboratory, Cold Spring Harbor, N.Y. (1982)]. ECTFPI 1 and 2 and ECTFPI 3 and 4 were annealed in the kinase buffer by incubating for 5 minutes at 70° C. and slow-cooling to room temperature. These fragments were cloned into pMON9308 which had been digested with NcoI/NsiI. PCR amplification was used to introduce a HindIII site as well as a TAA termination codon at the 3′ end of the TFPI gene. The PCR primers TPFIterm and TPFIterm 2 are shown below. The TFPI gene was then moved as a NCOI/HindIII fragment into pMON5766 (FIG. 12). The resultant plasmid was pMON6870.

```
N
c
o
 I       ECTFPl 1
catggctgattctgaAgaagatgaagaacaTacTa          [SEQ ID NO:2]
    cgactaagactTcttctacttcttgtAtgAtaatagtgA  [SEQ ID NO:3]

ECTFPl 2

N
                                s
       ECTFPl 3                 i
                                l
ttatcacTgatacTgaACtgccaccGctgaaactGatgca     [SEQ ID NO:4]
    ctatgActTGacggtggCgactttgaCt             [SEQ ID NO:5]

ECTFPl 4

HindIII
TFPIterm:  ataaca[aagctt]acatatttt           [SEQ ID NO:6]
              NcoI
TFPIterm2: atatat[ccatgg]ctgattct            [SEQ ID NO:7]
``` pMON6870 was digested with BglII/HindIII. This fragment, containing the expression cassette, was cloned into pMON6710 [Obukowicz et al., *Biochemistry* 29, 9737–9745 (1990)] which had been digested with BglII/HindIII. The resultant plasmid, pMON6875, includes the tac promoter, G10 leader from bacteriophage T7, met-ala TFPI, and the p22 transcriptional terminator. The plasmids were transformed into MON105 (rpoD+rpoH358) containing F′ from JM101 for the expression of TFPI protein.

Fermentation

Ten liter fermentations were run in M9minimal salts media supplemented with 20 g/l casamino acids in Biostad E fermentors (B. Braun). Fermentations were run at a temperature of 37° C., 1000 rpm agitation, an air flow rate of 15 l/min and 10 psi backpressure. pH was controlled at 7.0 with ammonium hydroxide. Residual glucose concentration in the fermentation broth was automatically controlled at 1.0+/−0.1 g/l. At an optical density of 46.0 at 550 nm, the temperature was shifted from 37° C. to 30° C. and isopropyl β-D thiogalactopyranoside (IPTG) was added to the fermentor to a final concentration of 1.0 mM. The culture was harvested four hours post-induction by concentration in an Amicon DC10L concentrator followed by centrifugation in a Beckman J2-21 centrifuge. The 10-liter fermentation yield 335–456 g (average of 376+/−46 g, n=6) wet weight of cell paste. The cell paste was frozen at −80° C. for further processing hereinbelow.

Isolation of inclusion bodies

Frozen *E. coli* cell paste was resuspended in cold Milli-Q water at a concentration of 75 g/l. The cells were thoroughly dispersed with a homogenizer (Ultra-Turrax model SD-45) for 30 minutes on ice. The cells were mechanically lysed by three passes through the Manton-Gaulin homogenizer (model 15 M-8TA) at 12,000 psi. Inclusion bodies were centrifuged in the Sorvall RC-2B centrifuge in the GSA rotor at 10,000 rpm (16,270×g) for 20 minutes. The supernatant was discarded. The inclusion body pellets were collected, resuspended in 1 l of cold Milli-Q water and dispersed with the Ultra-Turrax homogenizer for 30 minutes on ice. The inclusion bodies were cycled through the Manton-Gaulin homogenizer two more times on ice. Inclusion bodies were pelleted in the Sorvall RC-2B centrifuge as before. Approximately 60 mg of inclusion bodies were collected for every gram of *E. coli* cells lysed. The inclusion bodies were stored at −80° C.

Buffer preparation

All the buffers used for sulfonation and refolding of *E. coli* TFPI contained high concentrations of urea. Urea solutions were treated with Bio-Rad mixed bed resin AG501-X8 at room temperature for at least 20 minutes and filtered through 0.2 μm filter before mixing with buffers. All the solutions used for chromatography were 0.2 μm filtered and sonicated under house vacuum for about 10 minutes.

Sulfonation of inclusion bodies

One gm of inclusion bodies (wet weight) was dispersed in 40 ml of a solution containing 50 mM Tris/HCl, pH 8, and 7.5 M urea by homogenization and vortexing. After the inclusion bodies were largely dissolved, 800 mg of sodium sulfite was added and the mixture was shaken at room temperature for 30 minutes. Then, 400 mg of sodium dithionite was added and the mixture was shaken at 4° C. overnight. The solution dialyzed against 400 ml of a solution containing 20 mM Tris/HCl, pH 8, and 4 M urea for more than 5 hours at 4° C. using a Spectrapor #2 membrane. The dialyzed solution was centrifuged at 48,400×g for 1 hour, filtered through a 0.2 μm filter, divided into aliquots, and stored at −80° C.

Anion-exchange Chromatography of sulfonated TFPI

On a small scale, the sulfonated and dialyzed inclusion bodies were fractionated on a Mono Q HR5/5 anion exchange column. The column was pre-equilibrated in Q-buffer (20 mM Tris/HCl, pH 8, 6 M urea, 0.01% Brij 35 non-ionic surfactant) containing 0.15 M NaCl. Two ml of sulfonated inclusion bodies were loaded onto the column. The column was washed with 15 ml of the equilibration buffer and eluted with a 30-ml gradient (0.15–0.4 M NaCl) in Q-buffer. Fractions of 1 ml were collected. On a larger scale, 40 ml of sulfonated sample (equivalent to 0.56 g of wet weight inclusion body) was loaded onto a HiLoad Q Sepharose 16/10 anion exchange column pre-equilibrated in Q-buffer containing 0.15 M NaCl. The column was washed with 240 ml of equilibration buffer and then eluted with a 396-ml gradient (0.15–0.4 M NaCl) in Q-buffer. Nine ml fractions were collected. Both chromatographies were carried out on a Pharmacia FPLC system at room temperature.

Refold of sulfonated TFPI

The sulfonated, full-length TFPI pool from anion-exchange chromatography was diluted to an absorbance of 0.07 O.D. units at 280 nm with Q-buffer containing 0.3 M NaCl. Solid L-cysteine was added to a final concentration of 2 mM. The solution was incubated at room temperature for 24 hours, diluted 1:1 with water, 1 mM L-cysteine was added, incubated at room temperature for another 24 hours and then incubated at 4° C. for up to 8 days.

Mono S Chromatography of refold mixture

In analytical runs, 2 ml refold mixture was loaded onto a Mono S HR 5/5 cation exchange column pre-equilibrated in S-buffer (20 mM sodium phosphate, pH 6.4, 6 M urea). The column was washed with 10 ml of the equilibration buffer and eluted with a 70-ml gradient consisting of 0–0.7 M NaCl in S-buffer. One-ml fractions were collected. In preparative runs, the refold mixture was acidified to pH 4.5, concentrated 75-fold, and loaded onto a Mono S HR10/16 anion exchange column pre-equilibrated in S-buffer containing 0.3 M NaCl. The column was washed with 15-column volumes of the equilibration buffer and eluted with a 0.3–0.5 M NaCl gradient in S-buffer.

tissue factor-induced coagulation time assay

Conventional coagulation time assay was performed using a Fibrometer (Becton Dickinson) clot timer. Ninety μl of human pooled plasma was mixed with 10 μl of TFPI sample or control buffer in the well at 37° C. for 1 min and 0.2 ml of tissue factor (Simplastin Excel, diluted 1:60 into a solution containing 75 mM NaCl, 12.5 mM $CaCl_2$, and 0.5 mg/ml bovine serum albumin) was added to initiate the clotting reaction.

Amidolytic assay of factor $X_a$ inhibitory activity

Inhibitory activity against bovine factor $X_a$ of TFPI samples were assayed by conventional amidolysis of Spectrozme $X_a$ as described previously by Wun et al., *J. Biol. Chem.* 265, 16096–16101 (1990) except that the assay buffer consisted of 0.1 M Tris/HCl, pH 8.4, and 0.1% Triton X-100 non-ionic surfactant.

Protein determination

The concentration of protein was determined by absorbance at 280 nm and by quantitative amino acid analysis after HCl/vapor phase hydrolysis at 110° C. for 24 hours.

Sodium dodecyl sulfate-polyacrylamide gel electrophoresis (SDS-PAGE)

Daiichi precasted 10–20% gradient gels were used for SDS-PAGE. Samples are either unreduced and not boiled or reduced in 3.3% 2-mercaptoethanol and boiled for 3 minutes before electrophoresis. The gels were stained by Coomassie blue.

Results

Expression of TFPI in *E. coli*

Three vectors were constructed and used for expression of TFPI in *E. coli.* The first construct, pMON9308, which contained the original human TFPI cDNA sequence (except the initiating ATG) and the rec A promoter, achieved a very low level of expression (<0.5% of total cell protein). The second construct, pMON6870, which was similar to the first but was altered by introducing an alanine at the second position, by increasing the A-T richness of the 5'-end and by improving *E. coli* codon usage, did not significantly raise the expression level. The third construct pMON6875, which was similar to the second but used a tac promoter, achieved an expression level of approximately 5-10% of total cell protein and was used for further tests herein. The majority of TFPI (>90%) appeared be sequestered in inclusion bodies in disulfide-linked polymer form since a 32 kDa TFPI protein can be detected by SDS-PAGE and Western blotting only after reduction.

Figure 1A:
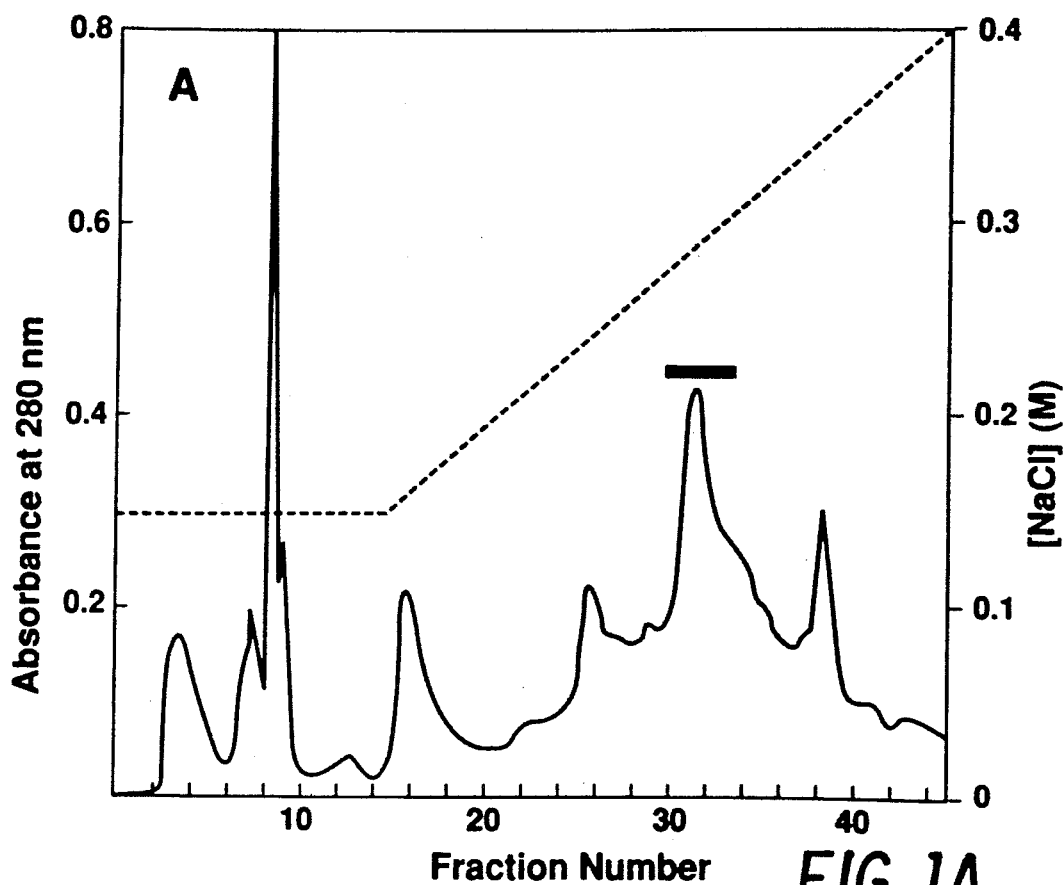
Figure 1B:
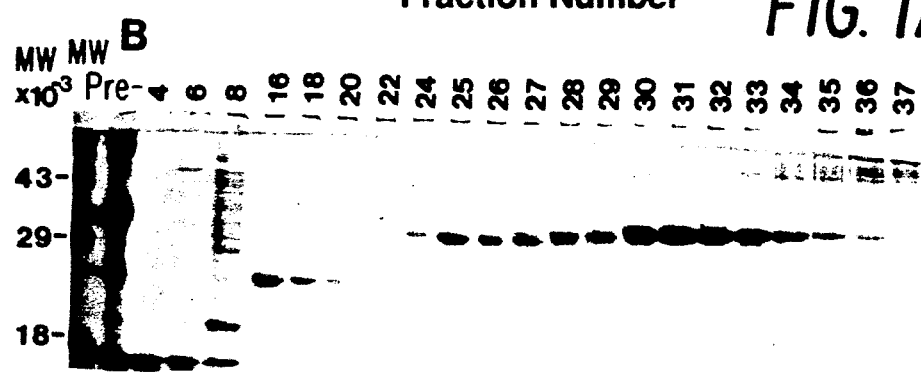
Figure 2A:
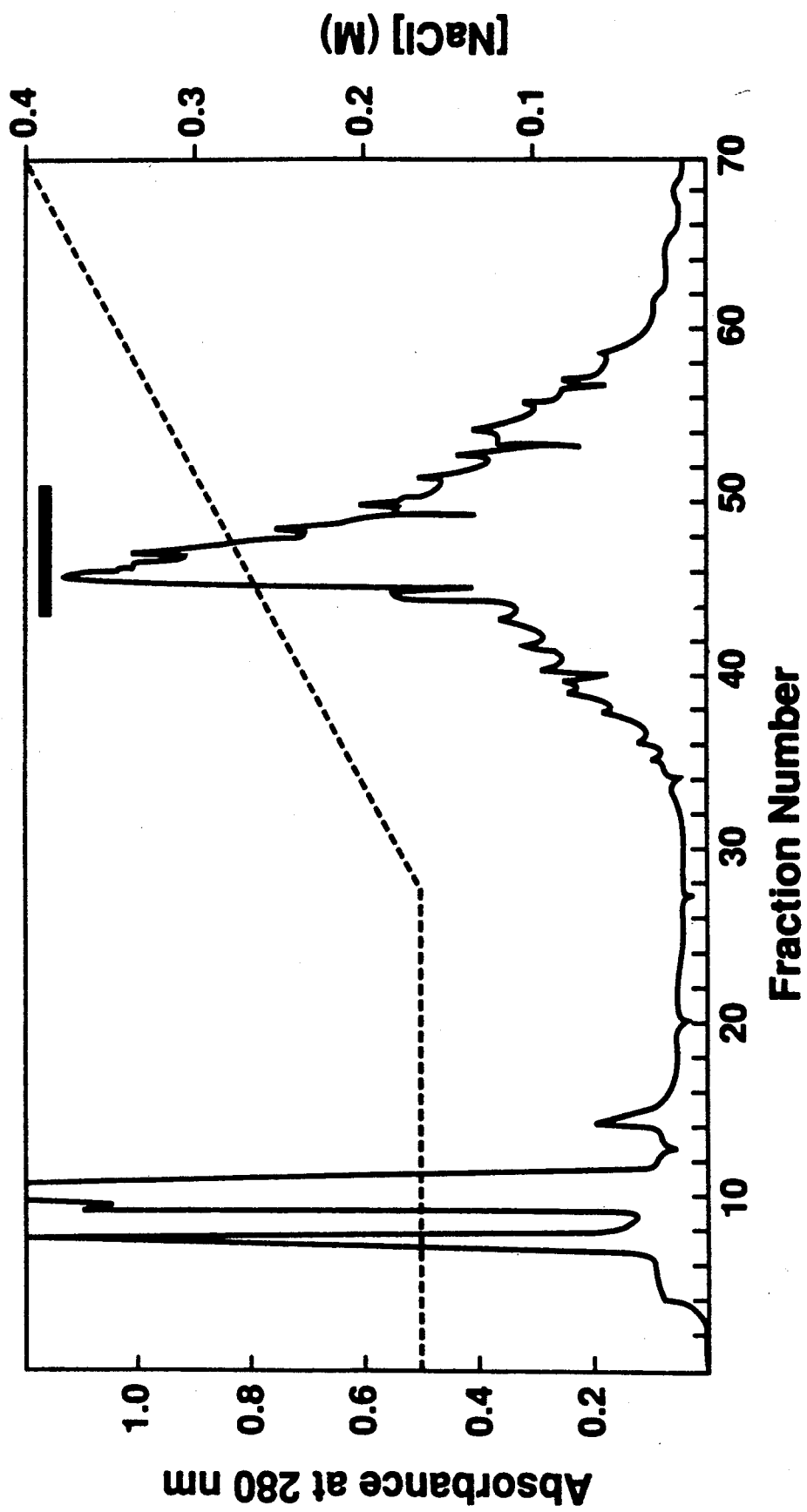
Figure 2B:
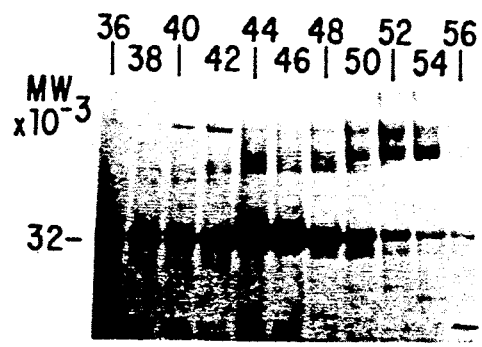

Sulfonation of inclusion body and purification of full-length sulfonated TFPI In initial tests, it was found that the *E. coli* lysate or the isolated inclusion bodies contained very little TFPI activity as measured by anti-factor $X_a$ and by tissue factor-induced coagulation time assays. Refolding of TFPI by reduction/re-oxidation and by sulfonation/disulfide interchange of the crude, solubilized inclusion bodies resulted in very low recovery of activity. Therefore, attempts were made to purify TFPI prior to refolding step, by sulfonation followed by anion exchange chromatography, taking advantage of the 18 added negatively charged groups on the sulfonated TFPI. The sulfonated inclusion bodies were first fractionated on an analytical Mono Q HR5/5 anion exchange column as shown in FIG. 1. The flow-through and early gradient fractions contained much of the contaminants *E. coli* protein and truncated TFPI protein (the latter are lower in molecular weight and are immuno-reactive against anti-TFPI-Ig). The full-length TFPI-S-sulfonate eluted at about 0.28 M NaCl. The fractionation of sulfonated inclusion bodies was scaled up 20 times using a Hiload Q Sepharose 16/10 anion exchanger as shown in FIG. 2. The chromatogram appeared somewhat different from that from Mono Q but the fractionation of the full-length TFPI-S-sulfonate appeared comparable as judged from SDS-PAGE (FIG. 1(B) and FIG. 2, inset).

Refold of TFPI-S-sulfonate

Figure 3:
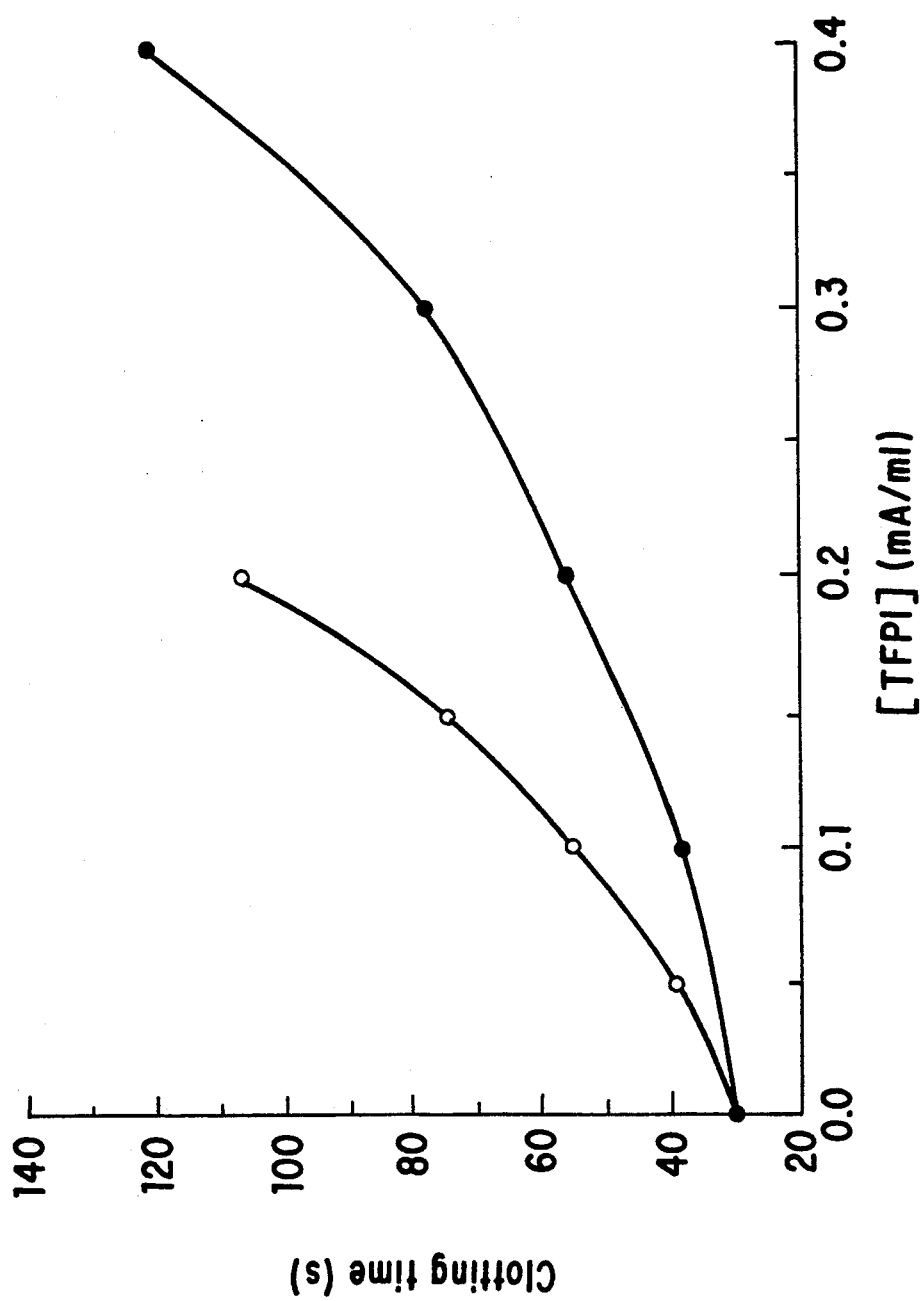

Sulfonated TFPI underwent spontaneous refolding and oxidation upon mixing with a suitable concentration of L-cysteine. The efficiency of refold as reflected in the increase of TFPI activity varies widely depending on the refold conditions. Numerous refold conditions were compared and optimized in terms of temperature, pH, urea, L-cysteine and protein concentration. A 2-stage refold process appeared to be the best. In the first stage, the full-length TFPI-S-sulfonate pool was adjusted to an absorbance at 280 nm of 0.07 O.D. units, 2 mM of fresh L-cysteine was added, and the mixture was incubated at room temperature for 24 hours. During this period, the TFPI activity increased from 0 to about 12% of full-length SK hepatoma TFPI which served as a standard for comparison. In the second stage, the solution was diluted 1:1 with water, and fresh L-cysteine was added to a final concentration of 1 mM. The mixture was incubated at room temperature for 24 hours, during which time the specific activity increased 2.6 fold to 3% that of SK TFPI. The solution was then left at 4° C. for several days during which time the TFPI activity increased to about 60% that of SK TFPI in the initial 24 hours followed by a slow increase to about 68% of SK TFPI (FIG. 3).

Fractionation of refold mixture by Mono S chromatography

Figure 4A:
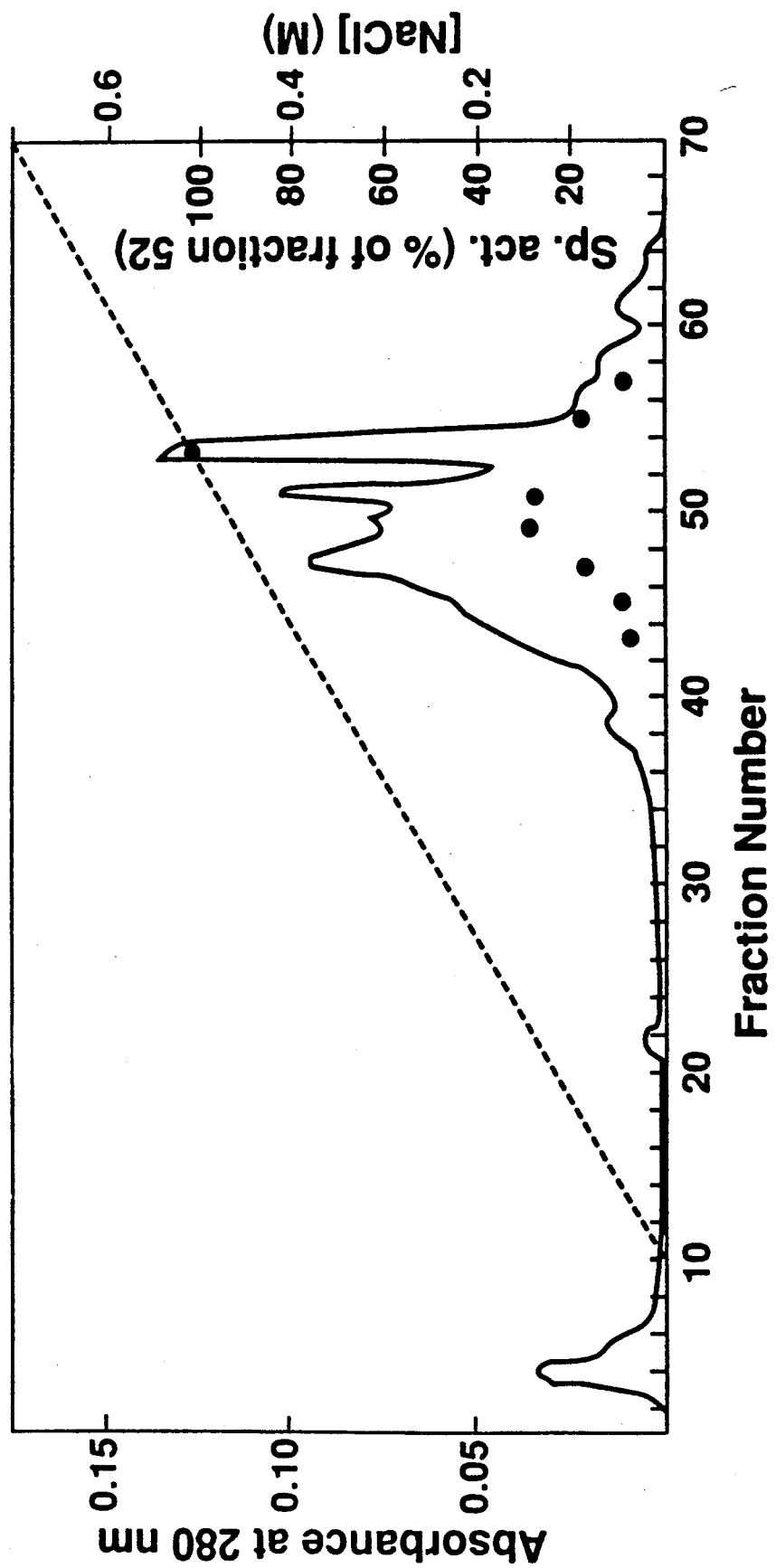
Figure 4B:
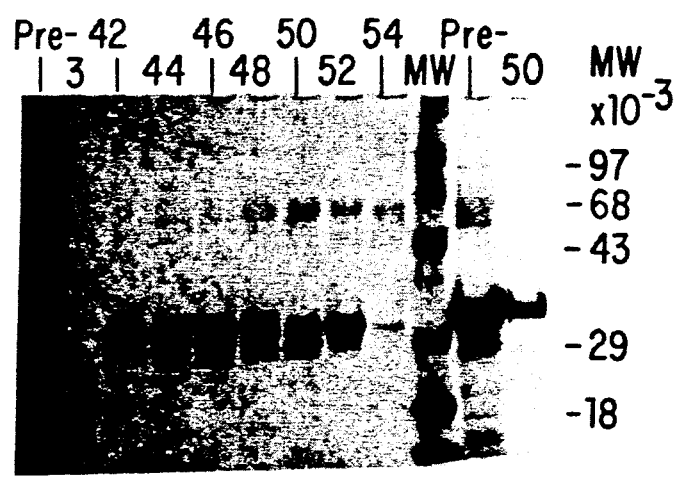
Figure 5A:
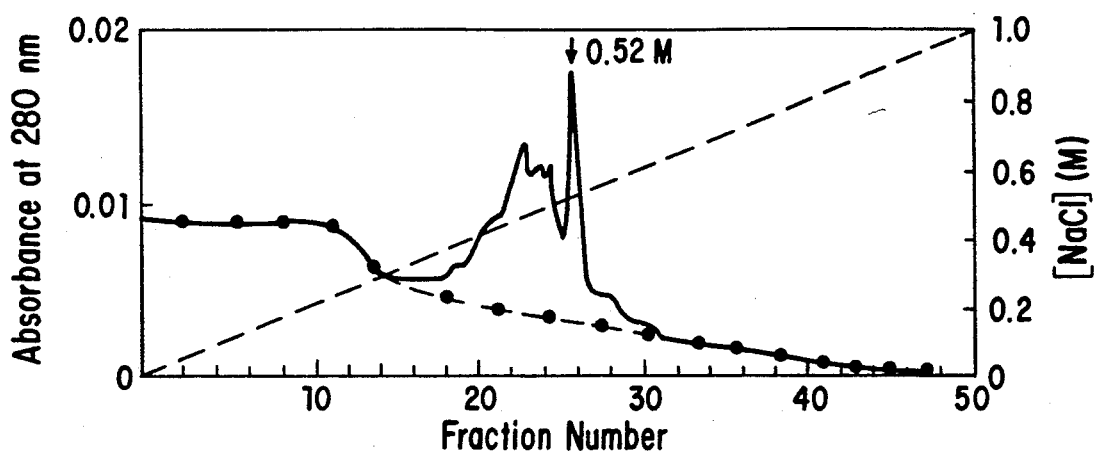
Figure 5B:
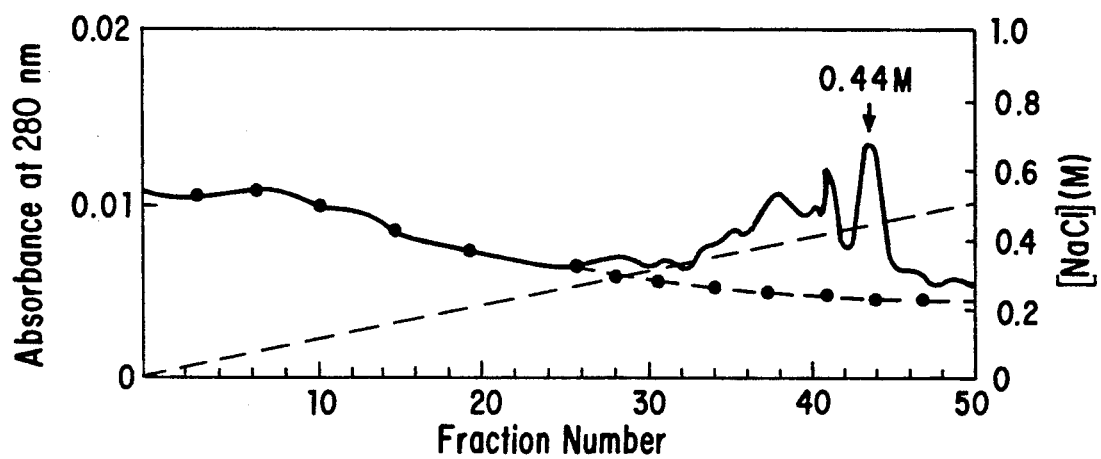
Figure 5C:
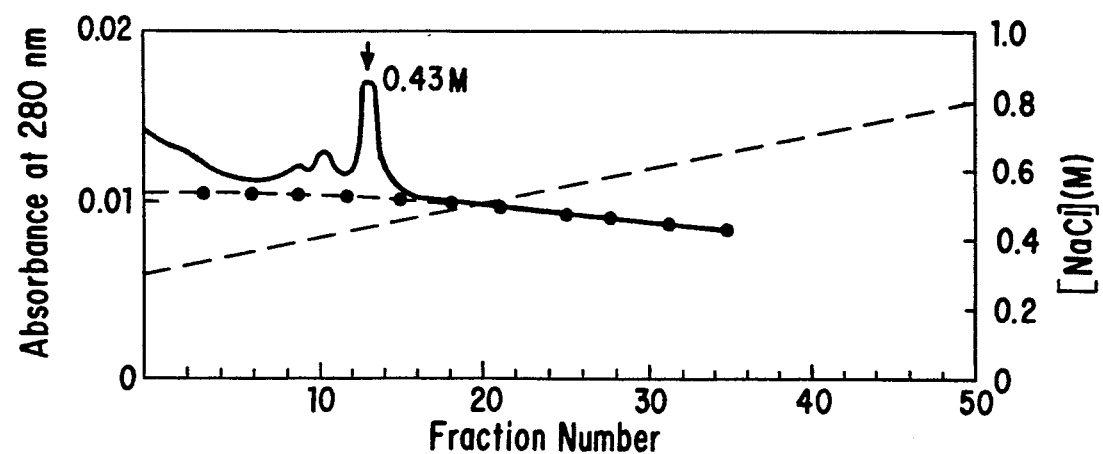

The specific activity of the refold mixture was lower than the purified mammalian SK TFPI which suggests that the former may contain both correctly folded and misfolded molecules or only partially active misfolded molecules. The refold mixture was fractionated on an analytical Mono S cation exchange column as shown in FIG. 4. When the UV-absorbing fractions were analyzed for TFPI activity, the highest specific activity was associated with a sharp peak (fraction 52) eluted at 0.52 M NaCl. All the other fractions had a specific activity less than 30% that of fraction 52. SDS-PAGE analysis (FIG. 4, inset) showed that fraction 52 contained a sharp band and all other fractions, together with pre-column refold mixture, consisted of diffuse, multiple bands under nonreducing condition. The diffuse bands are apparently mainly full-length TFPI in various folded forms since they become sharp-banded upon reduction (see the last two lanes on the right). FIG. 5 shows the optimization of the Mono S chromatography on an analytical scale. By making the gradient more shallow, the resolution of the peaks became better and all the protein peaks appeared to elute at lower NaCl concentrations [FIGS. 5 (A) and (B)]. Further, it was possible to wash out the majority of the low-activity peaks with 10 column volumes of 0.3 M NaCl before eluting the active peak with a shadow gradient.

Figure 6A:
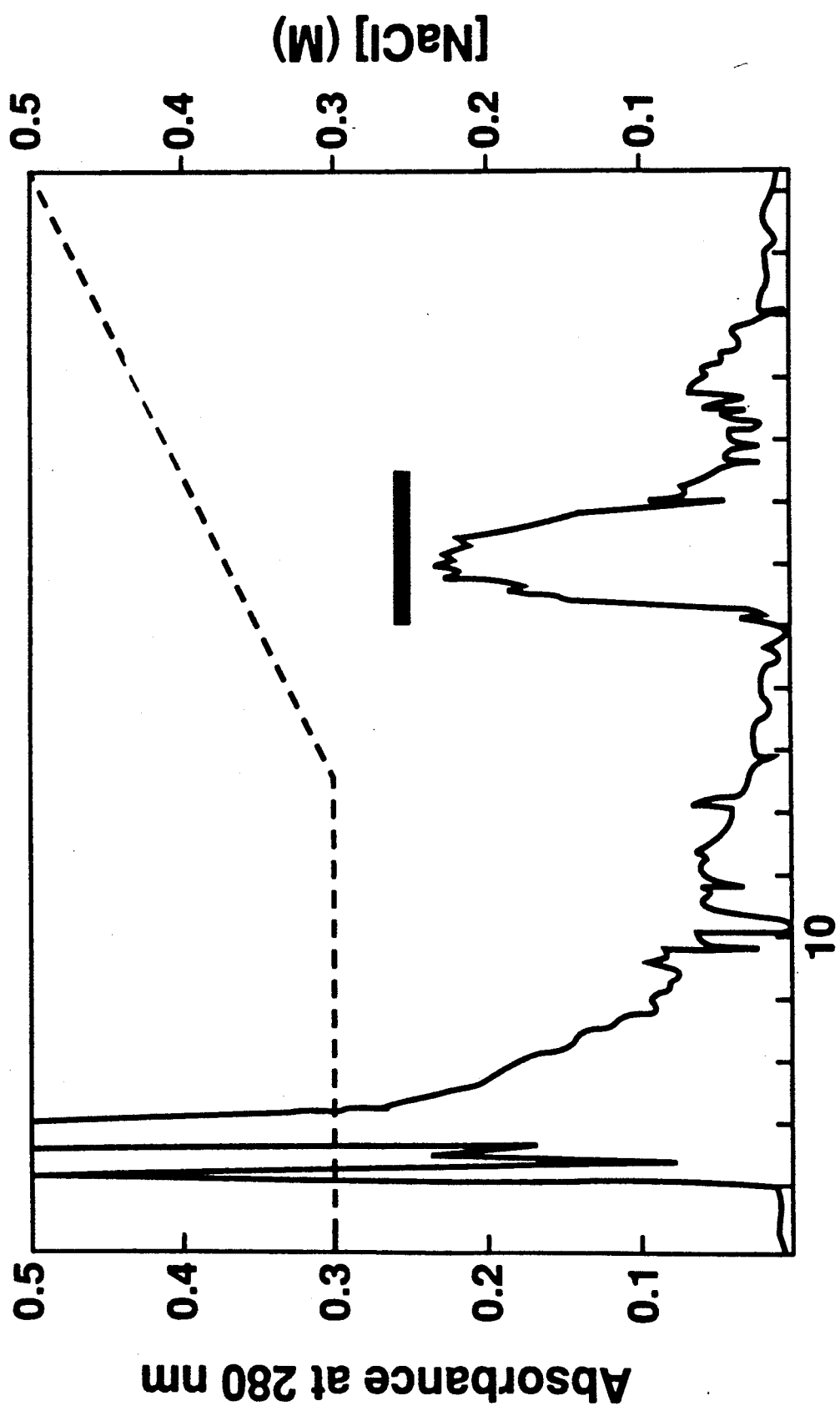
Figure 6B:
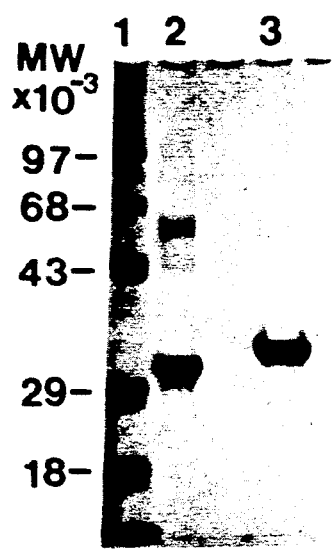

Based on the above results, the chromatography was scaled up using a Mono S HR10/16 cation exchange column as shown in FIG. 6. The column was washed with 15 column volumes of 0.3 M NaCl Which essentially washed out all low activity peaks. Afterwards, a shadow gradient eluted a peak of protein that contained the active TFPI. SDS-PAGE analysis (FIG. 6, inset) shows that the peak gave a sharp band under either reducing or non-reducing conditions. The reduced and boiled protein migrated somewhat slower in SDS-PAGE.

Stoichiometry of the interaction of refolded TFPI with factor $X_a$

Figure 7:
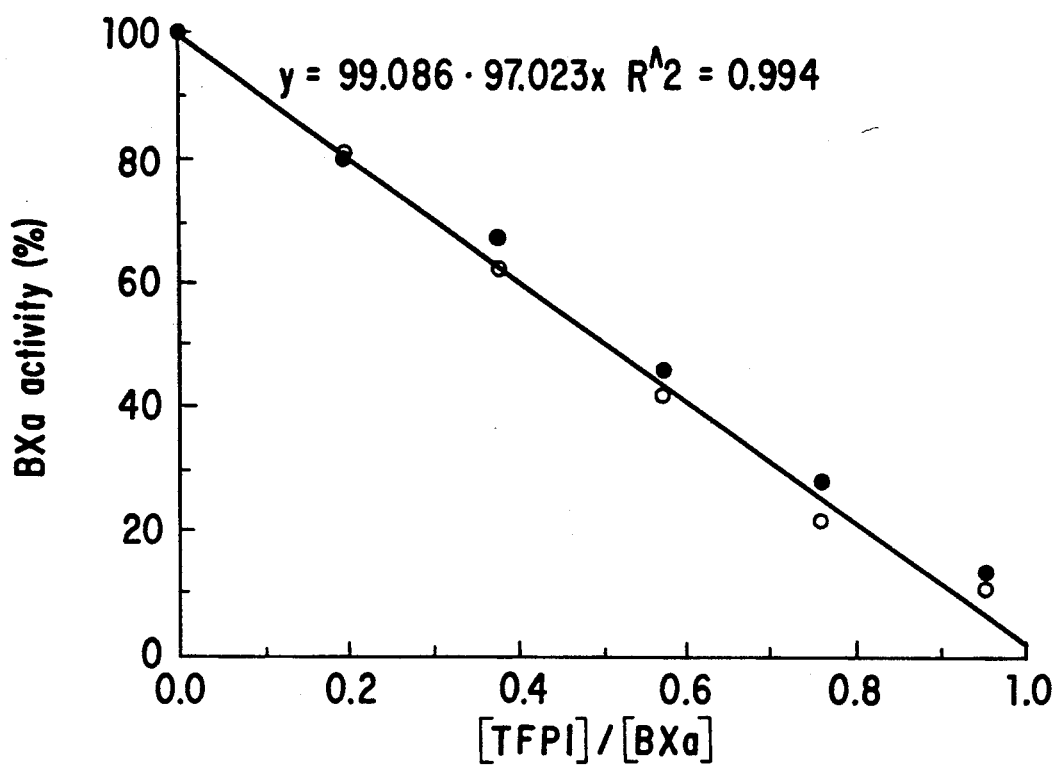

Inhibition of bovine factor $X_a$ by the active refolded *E. coli* TFPI was examined by measuring the residual amidolytic activity using Spectrozyme $X_a$. As shown in FIG. 7, the molar ration of TFPI to bovine factor $X_a$ that resulted in the complete inhibition of the latter was 1:1 (open circle). For comparison, the stoichiometry of interaction of SK TFPI with bovine factor $X_a$ was also 1:1 (closed circle).

Inhibition of tissue factor-induced coagulation

Figure 8:
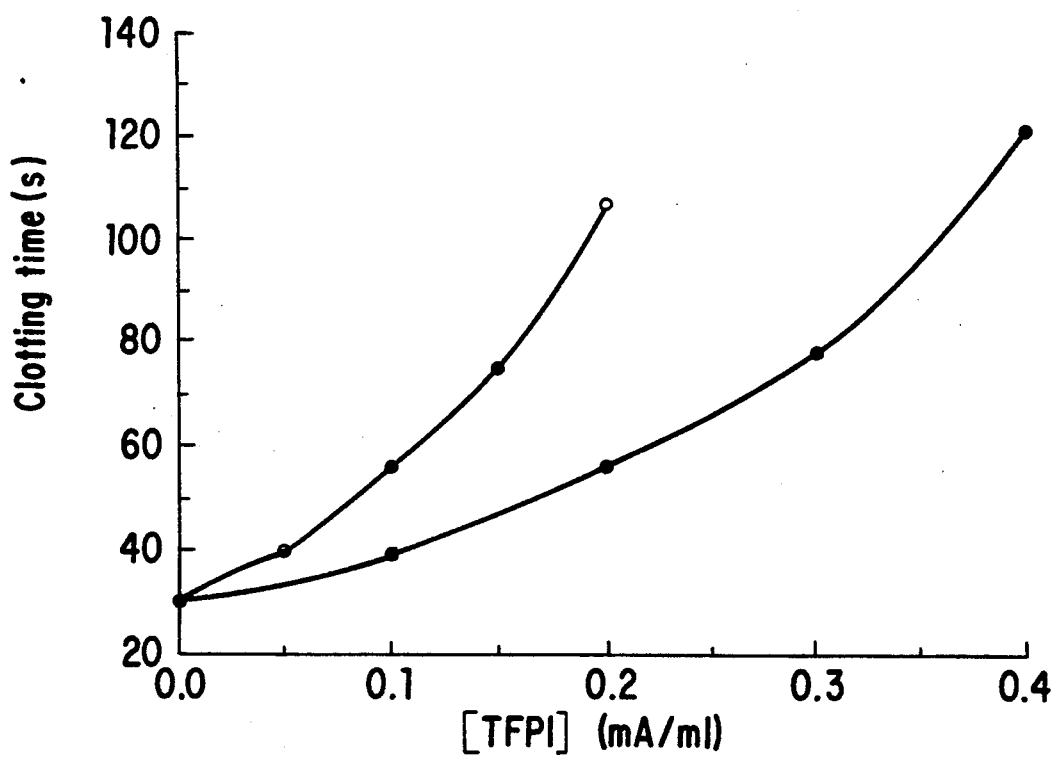

The ability of the active, refolded *E. coli* TFPI to inhibit tissue factor-induced coagulation in human plasma was compared with that of the purified SK TFPI. As shown in FIG. 8, the activity of the *E. coli* TFPI was approximately two fold more active than SK TFPI on a per mol basis as judged from the concentrations of each TFPI that produce the same prolongation of clotting time.

TABLE 1
Summary of refold and purification of active *E. coli* TFPI.

|  | $A_{280}$ nm | Volume (ml) | Total $A_{280}$ nm | Specific activity[a] (SK unit/mA) | Yield (%) |
|---|---|---|---|---|---|
| Starting material 0.56 g inclusion body | — | — | — | — | — |
| Sulfonated inclusion body | 6.1 | 25 | 153 | 0 | — |
| HiLoad Q pool | 0.8 | 46 | 37 | 0 | — |
| refold mixture | 0.035 | 1050 | 37 | 0.66 | 100 |
| Mono S pool | 0.142 | 48 | 6.8 | 2.0 | 18 |

[a]Specific activity was determined by tissue factor-incuced coagulation time assay as described in METHODS. One SK unit defined as the amount of activity equivalent to that produced by 1mA (1 × 10$^{-3}$ absorbance unit at 280 nm or 1.31 ug) of purified full-length SK hepatoma TFPI.

EXAMPLE II

Inclusion bodies as prepared in EXAMPLE I, above, were subjected to the following alternate purification process:

Pre-Refold Cation Exchange Chromatography

Washed inclusion body pellets were suspended in 8 M Urea, 0.05 M NaHPO$_4$, 5% B-Mercaptoethanol (BME), pH 8.5 (60 ml buffer for each 1 L broth equivalent of inclusion bodies). The solution was gently agitated using an Adams Nutator shaking table (Baxter/Scientific Products) for 1 hour at 6°–8° C. and centrifuged at 37,000×G for 2 hours. The supernatant was diluted 10-fold with 6 M Urea, 0.05 M NaHPO$_4$, 5% BME, pH 7.0 (Equilibration Buffer), and filtered through 0.22 μm Durapore PVDF filter media (Polyvinylidene difluoride microfiltration membrane filter from Millipore). The clarified solution was loaded onto a column of SP-650-S cation exchange gel resin (Toyopearl, from TosoHaas, Tosoh Corp. and Rohm and Haas Co.) equilibrated with at least 15 column volumes of equilibration buffer. For small scale work, a 4.4×16 cm column was loaded with the equivalent of 5 L broth. For larger scale work, a 9.0×18 cm column was loaded with the equivalent of 15-20 L broth. After loading at a linear flow rate of 10-15 cm/h, the column was washed with 10 column volumes of equilibration buffer. The column was eluted with a linear gradient from 0 to 0.14 M NaCl in equilibration buffer at a rate of 1 mM NaCl/minute. The NaCl concentration Was held at 0.14 M for 2 column volumes while the main peak eluted. 25 ml fractions were collected and analyzed by RP-HPLC and SDS-PAGE for TFPI content before pooling. Acceptable fractions were concentrated to 20 mg/ml using stirred cells (Amicon) and buffer exchanged into 6 M Urea, 50 mM NaOAc, 0.5 M NaCl, pH 4.5 using Bio-Rad P6DG desalting gel. These fractions were then stored at −40° C. until needed.

Refolding of TFPI

Frozen fractions from above were thawed and the protein concentration adjusted to 0.3 mg/ml protein in a buffer consisting of 6 M Urea, 0.05 M NaOAc, 0.5 M NaCl, 0.05 M NaPO$_4$, pH 10.5. L-Cysteine (Sigma) was added to give a concentration of 0.1 mM using freshly prepared 0.1 M L-Cysteine in 6 M Urea, 50 mM NaOAc, 0.5 M NaCl, pH 4.5. After mixing for 10 minutes, the solution was incubated without stirring at 10°–15° C. for 48–72 hours. The reaction was monitored for prothrombin time (PT) activity and when the PT activity reached a plateau, the refold was terminated by adjusting the pH to 5.0 with 2.5 N HCl and freezing at −40° C.

Purification of Active TFPI from Crude Refold Mixture

Crude refold mixture was concentrated in stirred cells using Amicon YM10 membranes to 5 mg/ml, and then buffer exchanged into 6 M Urea, 0.05 M NaOAc, pH 4.5 using Bio-Rad P6DG resin. For small scale chromatography, 35 mg protein was loaded onto a Pharmicia MONO-S HR10/10 column equilibrated with 2 M Urea, 50 mM NaOAc, pH 6.0. For larger scale preparation, 500 mg of protein was loaded onto a Pharmacia HiLoad 26/10 S Sepharose equilibrated in the same buffer. Elution was effected by rapidly increasing the NaCl concentration to 460 mM (33 mM/min) and held for 10 column volumes while the main peak eluted. Fraction collection was initiated at the beginning of the isocratic step, with the fractions of highest specific activity eluting on the trailing side of the main protein peak.

Fractions were pooled based on specific activity and diluted with four volumes of 6 M Urea, 20 mM NaOAc, pH 6.0 before being applied to a Pharmacia MONO-S HR10/10 column equilibrated with the same buffer. Elution consisted of the same buffer containing NaCl, using a linear gradient of 0–600 mM NaCl at a rate of 3.6 mM/minute. Fractions of 2.5 mL were collected and pooled based on PT specific activity and SDS PAGE. Reprocessing of fractions using the same MONO-S chromatography in 6 M urea resulted in the recovery of additional high specific activity protein.

The TFPI products produced by embodiments (A) and (B) according to the method of the invention in EXAMPLES I and II, above, were further assayed by several methods with results as follows:

1. Polyacrylamide Gel Electrophoresis Analysis

Figure 9:
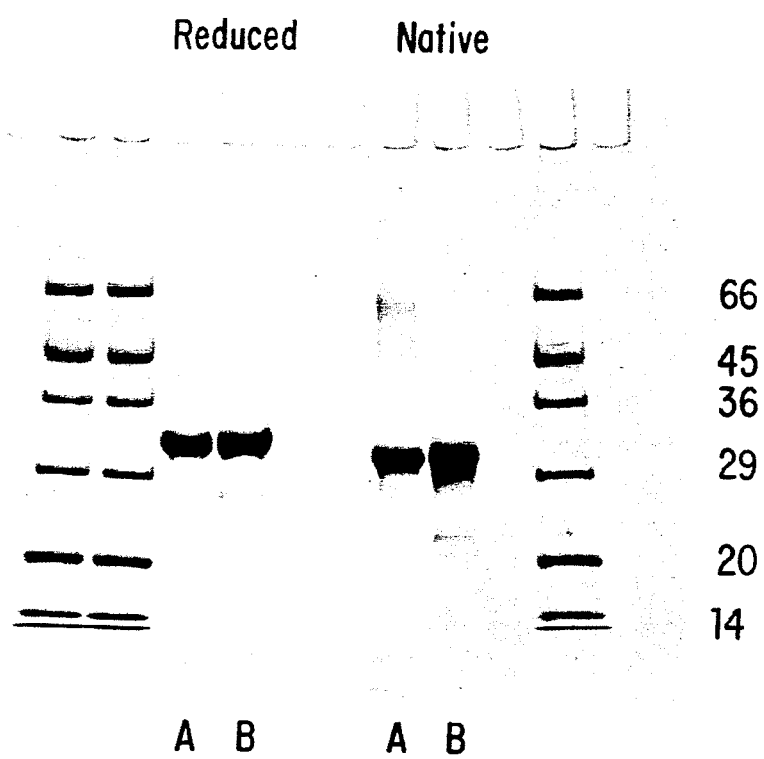
Figure 10:
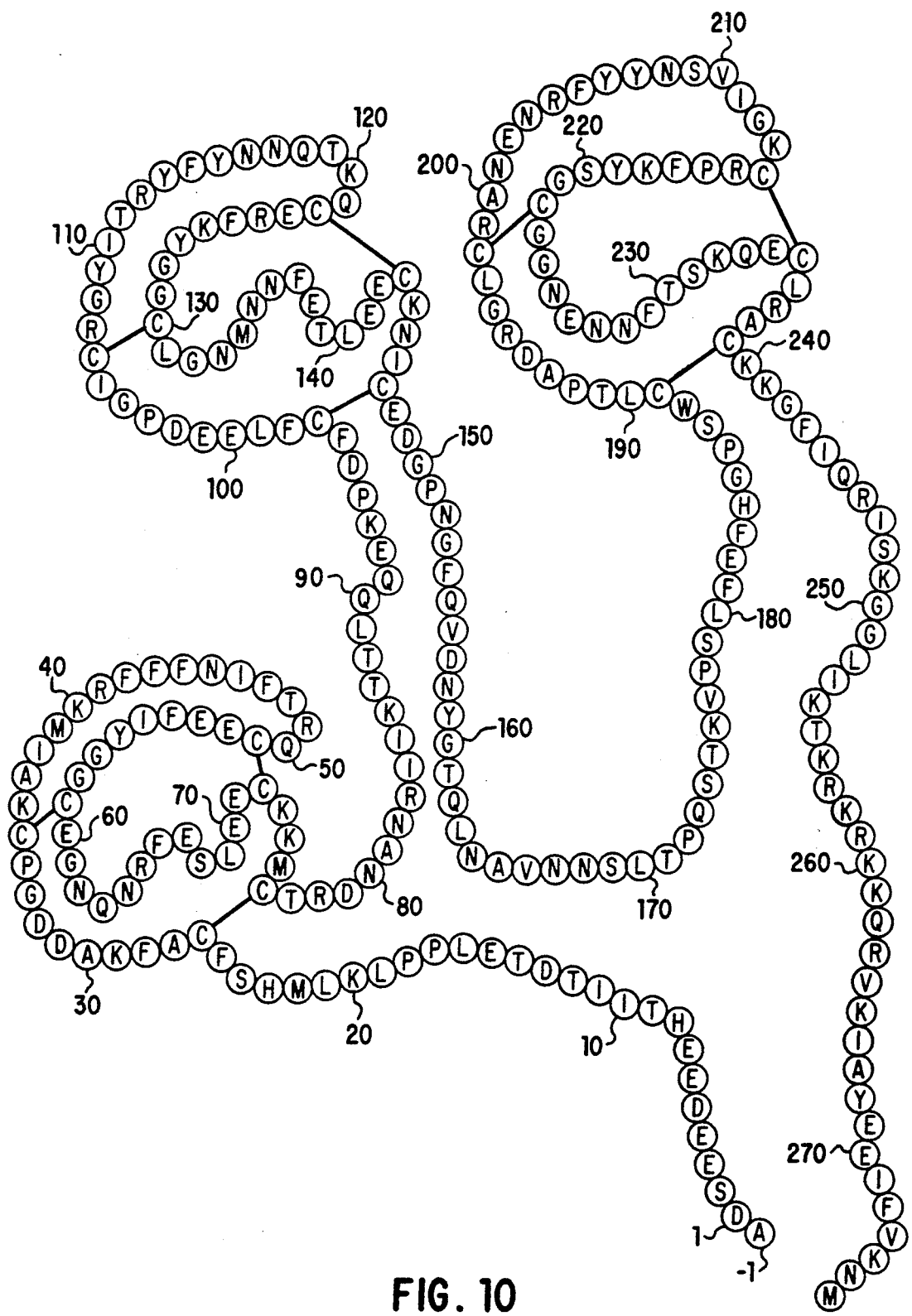
FIG. 10 is a schematic diagram of the secondary structure showing the sulfhydryl bonding for the three Kunitz domains of the 277 amino acid residue ala-TFPI [SEQ ID NO:1]. Residues 1 to 276 correspond to the published sequence of TFPI (LACI), as described hereinbefore, and the N-terminal alanine is assigned −1.

The primary band of TFPI from both processes was identical on reduced and native gels. However on native gels the TFPI from the EXAMPLE I process had a higher content of dimer species, whereas the TFPI produced from the EXAMPLE II process had a higher content of lower molecular weight (C-terminally truncated) species. See FIG. 9.

2. Reversed Phase Analysis

A reversed phase analysis of TFPI produced by the EXAMPLE I process revealed a single sharp peak (indicating high purity) whereas TFPI produced by the EXAMPLE II process revealed a primary and a secondary peak (indicated a significant degree of heterogeneity). TFPI produced from the SK Hep mammalian system revealed a broad primary peak and several secondary peaks (indicating a significant degree of heterogeneity).

3. Cation Exchange Analysis

A cation exchange analysis did not reveal any differences between TFPI produced from the EXAMPLES I and II processes. A single symmetrical peak was produced in both cases. However, crude SK Hep TFPI, characterized in the same manner, yielded a primary and a secondary peak, indicative of heterogeneity.

4. Electrospray Mass Spectral Analysis

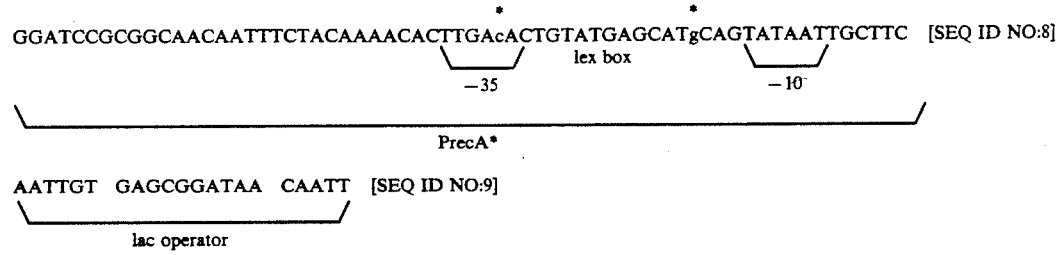

Electrospray analysis of TFPI indicated that the mass of the primary component of TFPI produced from both processes was the same. However, the material produced from the EXAMPLE II process contained up to 30% heterogeneous species whereas the material produced from the EXAMPLE I process appeared to be essentially homogeneous (>95%). Electrospray analysis of SK Hep TFPI can not be accomplished because of the high extent of heterogeneity of the carbohydrate chains.

EXAMPLE III

This example illustrates the construction of an alternate expression vector containing the cDNA coding for TFPI, namely plasmid pMON6890. pMON6890 contains a hybrid promoter consisting of an altered recA promoter in conjunction with the lac operator. The following sequence was assembled to optimize the −35 region of the recA promoter and to eliminate lexA (repressor) binding.

The base change indicated in the −35 region of PrecA made it identical to the −35 consensus sequence. The base substitution indicated in the lex box (site where lexA repressor binds) was shown to result in constitutive recA expression. Addition of the lac operator sequence placed the recA promoter under control of the lac repressor. This sequence was cloned as a BamHI/XbaI fragment into pMON6870 (as described in EXAMPLE I, above) which had been digested BamHI/XbaI. The TFPI expression vector 6890 is a pBR327 based plasmid containing the reclac promoter, the bacteriophage T7 gene 10 leader, and the M13 origin of replication.

Various other examples will be apparent to the person skilled in the art after reading the present disclosure without departing from the spirit and scope of the invention. It is intended that all such other examples be included within the scope of the appended claims.

What is claimed is:

1. A method for the production of a non-glycosylated form of tissue pathway inhibitor (SEQ ID No. 1) which comprises culturing under fermentation conditions sufficient to produce TFPI *E. coli* cells which have been transformed with a replicable expression vector containing the cDNA coding for said TFPI, harvesting the *E. coli* cells, isolating the inclusion bodies from the harvested *E. coli* cells and subjecting the inclusion bodies to a stepwise purification comprising either series (A) or series (B) as follows:

(A)

(1) subjecting the inclusion bodies to sulfitolysis to form TFPI-sulfonate,
(2) purifying TFPI-S sulfonate by anion exchange chromatography,
(3) refolding TFPI-S sulfonate by disulfide interchange reaction, and (4) purifying active refolded TFPI by cation exchange chromatography, or (B)

(1) subjecting the inclusion bodies to reduction with β-mercaptoethanol in urea to form reduced TFPI, (2) purifying the reduced TFPI by cation exchange chromatography, (3) refolding reduced TFPI by disulfide interchange reaction in urea, and (4) purifying the active refolded TFPI by cation exchange chromatography.

2. The method of claim 1 in which the sulfitolysis is carried out by reaction of the inclusion bodies with sodium sulfite and sodium dithionite.

3. The method of claim 1 in which the anion exchange chromatography is carried out by chromatographing the TFPI-S-sulfonate on a HPLC column of quaternary amine anion exchange resin.

4. The method of claim 1 in which the refolding of TFPI-S-sulfonate is carried out by reaction of said TFPI-S-sulfonate with L-cysteine.

5. The method of claim 1 in which the cation exchange chromatography is carried out by chromatographing the refolded TFPI on a HPLC column of sulfonic acid group cation exchange resin.

6. The method of claim 1 in which the sulfitolysis is carried out by reaction of the inclusion bodies with sodium sulfite and sodium dithionite, the anion exchange chromatography is carried out by chromatographing the TFPI-S-sulfonate on a HPLC column of quaternary amine anion exchange resin, the refolding is carried out by reaction of said TFPI-S-sulfonate with L-cysteine, and the anion exchange chromatography is carried out by chromatographing the refolded TFPI on a HPLC column of sulfonic acid cation exchange resin.

* * * * *

UNITED STATES PATENT AND TRADEMARK OFFICE
CERTIFICATE OF CORRECTION

PATENT NO. : 5,212,091

DATED : May 18, 1993

INVENTOR(S) : Judy A. Diaz, Mark E. Gustafson, Tze-Chein Wun

It is certified that error appears in the above-identified patent and that said Letters Patent is hereby corrected as shown below:

In col. 20, line 64,"TFPI" should read --TFPI-S--.

Signed and Sealed this

Twenty-ninth Day of November, 1994

Attest:

BRUCE LEHMAN

Attesting Officer

Commissioner of Patents and Trademarks